United States Patent [19]

Melnick et al.

[11] 4,225,669

[45] Sep. 30, 1980

[54] STAINING AND ANALYSIS OF BACTERIA

[76] Inventors: Joseph L. Melnick; Craig Wallis, both of Houston, Tex.

[21] Appl. No.: 33,900

[22] Filed: Apr. 27, 1979

Related U.S. Application Data

[63] Continuation-in-part of Ser. No. 945,197, Sep. 25, 1978, abandoned.

[51] Int. Cl.$^3$ .................. C12Q 1/29; C12Q 1/18; C12Q 1/04; C12Q 1/06
[52] U.S. Cl. ........................ 435/29; 8/94.11; 435/32; 435/34; 435/39
[58] Field of Search .............. 435/4, 29, 32, 33, 34, 435/36, 37, 38, 39, 40, 243; 424/3, 7; 8/94.11

[56]  References Cited

U.S. PATENT DOCUMENTS

| 2,967,132 | 1/1961 | Sachs | 435/32 |
|---|---|---|---|
| 3,043,751 | 7/1962 | Goldman | 435/29 |
| 3,068,154 | 12/1962 | Majors | 435/39 |
| 3,415,718 | 12/1968 | Forkman et al. | 435/36 |
| 3,496,066 | 2/1970 | Berger et al. | 435/29 |
| 3,509,872 | 5/1970 | Trahan | 128/2 |
| 3,532,603 | 10/1970 | Freake | 435/39 |
| 3,621,016 | 11/1971 | Berger et al. | 260/240.1 |
| 3,846,242 | 11/1974 | Ernst | 435/32 |

Primary Examiner—Robert J. Warden

Attorney, Agent, or Firm—Watson, Leavenworth, Kelton & Taggart

[57] ABSTRACT

A bacterial staining composition and methods of analysis of both gram-negative and gram-positive bacteria are disclosed. The composition comprises a chelating agent and a basic dye, both of which are operative at a pH above about 7.0. Bacterial staining may be effected by contacting either concentrated or fluidly suspended bacteria with the composition at a neutral or basic pH. Bacteria stained with the composition and concentrated by filtration, centrifugation or the like are readily visible and their presence in a specimen may, thus, be rapidly detected. The gradations of color of the stained, concentrated bacteria correspond to the number of bacteria and semi-quantitative analysis of the bacteria may be effected by comparison with a standard. Differentiation of gram-negative and gram-positive bacteria may be accomplished by treating the stained bacteria with an organic acid wash having a pH of about 2.5 to 2.6. Such a wash completely decolorizes only stained gram-positive bacteria. Finally, a method for determining bacterial susceptibility to antimicrobial agents is provided which comprises incubating bacteria with an antimicrobial agent, staining the bacteria and thereafter comparing the color gradation of the stained, concentrated bacteria with a control or standard.

52 Claims, No Drawings

STAINING AND ANALYSIS OF BACTERIA

This is a continuation-in-part of application Ser. No. 945,197, filed on Sept. 25, 1978 now abandoned.

BACKGROUND OF THE INVENTION

A need exists for a method of rapidly detecting bacteria in fluids from many sources. Of particular significance is the need for rapid detection of pathogenic bacteria in physiological fluid specimens, such as blood, urine and the like. Moreover, a need exists for a method for rapidly determining the susceptibility of such infecting bacteria.

Urine specimens in general form the major part of the work load of the diagnostic microbiology laboratory. By far the most common urological disease is urinary tract infection. In fact, in many hospitals, bacteriuria is the most common form of nosocomial infection, often following the use of in-dwelling catheters and various surgical procedures. The volume of specimens requiring bacteriuria screening is further increased by the need to repeat the tests to insure accurate diagnosis where their reliability may have been reduced due to contamination of the specimen during collection. A further problem with diagnosis and treatment of bacteriuria is the frequent lack of correlation between a patient's symptomatic response to antimicrobial treatment and successful treatment. In order to insure that the prescribed antimicrobial agent is in fact effective, repeated tests during therapy are required. The need for simple, rapid bacteriuria tests is thus clear. Moreover, in view of the frequent unsuspected asymptomatic occurrences of urinary tract infections among children, pregnant women, diabetics and geriatric populations, diagnosis of which may require collection and testing of several specimens, bacteriuria tests must be sufficiently simple and economical to permit routine performance. A need thus exists for rapid, inexpensive screening tests to facilitate diagnosis and insure proper treatment of urinary tract infections.

Rapid tests for detection of bacteria in blood are also needed, in view of the high mortality rate associated with septicemia and bacteremia. Prompt detection of the disease permits early administration of an appropriate antibiotic thus greatly improving the chances for survival.

According to conventional techniques, bacterial infections in specimens, such as blood, urine, spinal fluid and the like, are detected by diluting a specimen with culture media and incubating the diluted specimen at 36° C. The appearance of turbidity manifests bacterial growth. However, relatively extended periods of incubation are required since turbidity due to bacterial growth is difficult to distinguish from turbidity due to the presence of blood cells or contaminants in the specimen and from turbidity caused by precipitate formation. Substantial increases in turbidity following incubation periods of about 24 hours indicate bacterial growth.

Another very important procedure in the clinical laboratory is determination of antimicrobial susceptibilities. The principal methods presently employed to determine susceptibility of a micro-organism to an antibiotic include dilution tests, such as the broth tube and agar plate procedures and agar diffusion tests, utilizing antibiotic-impregnated discs. Typically, such methods require incubation periods of 16 to 18 hours before the inhibitory effect of an antimicrobial agent can be accurately assessed. Furthermore, such tests often are time consuming, relatively expensive and must be performed by skilled laboratory personnel.

Although staining techniques are known in clinical microbiology, such techniques are typically employed to stain dried bacterial smears on slides rather than in fluid specimens. In the practice of such prior art staining techniques, a dried bacterial smear on a slide is treated with a reagent which stains the bacteria in a manner which permits ready microscopic examination thereof. Thus, expensive equipment and skilled microbiologists are required to perform such analyses.

In addition to bacterial examination of body fluids, it is often necessary to analyze the bacterial content of other fluid specimens, such as water and pharmaceutical products. The need for rapid, simple, inexpensive and accurate methods for detecting and analyzing bacteria in body fluids and other fluid specimens is thus evident.

It has now unexpectedly been discovered that both gram-negative and gram-positive living bacteria can be stained for simple, rapid analysis by means of the composition of the present invention. Concentrated bacteria stained with the composition are readily visible and can thus be rapidly detected without resort to microscopic examination or specially trained personnel. Moreover, antimicrobial susceptibility of bacteria can be determined rapidly and simply by means of the present invention. Further, it was unexpectedly found that inexpensive, simple and rapid quantitative analyses of bacteria are possible employing the present staining composition. Finally by means of the present invention, it is possible to differentiate gram-negative and gram-positive bacteria.

SUMMARY OF THE INVENTION

A composition for staining both gram-negative and gram-positive bacteria is provided. The composition comprises a chelating agent operative in the basic pH range and a basic dye capable of staining bacteria at a basic pH. Bacteria are stained when contacted with the composition at a pH above about 7.0. Bacteria which are stained with the composition and concentrated become readily visible, and may thus be detected.

Semi-quantitative analysis of bacteria may be accomplished by comparing the gradation of color developed in concentrated stained bacteria, with a nomograph or other calibrated standard. Semi-qualitative analysis of the stained bacteria may be effected by means of an organic acid wash having a pH of about 2.5 or 2.6, since such an acid wash will completely decolorize only gram-positive bacteria stained with the composition.

By incubating bacteria with an antimicrobial agent prior to staining with the composition of the invention, the susceptability of the bacteria to the agent can be determined. The relative intensity of the color of stained, concentrated bacteria, thus treated, will be related to the effectiveness of the agent employed.

The invention is particularly useful in laboratory screening of body fluids and other physiological fluid specimens.

DETAILED DESCRIPTION OF THE INVENTION

This invention relates to compositions useful for staining both gram-negative and gram-positive bacteria and to various methods of detecting and analyzing bacteria in fluids. Broadly stated, the staining composition of the invention comprises a chelating agent and a dye. Bacteria contacted with this composition at a pH above about 7.0 are stained and upon concentration become readily visible.

Since the color intensity of stained concentrated bacteria is correlated with the number of bacteria in a sample, semi-quantitative analysis of bacteria may be accomplished by comparing the intensity of the color developed in the stained concentrated bacteria with a nomograph or other known standard. When concentration of the bacteria is effected by deposition of bacteria on a semi-permeable membrane, dye not associated with the bacteria, which may interfere with an accurate detection and quantitation of bacterial presence, may be removed by means of an organic acid wash having a pH in the range of about 2.7 to 4.0. If bacteria are incubated with an antimicrobial agent for a brief period prior to contact with the staining composition, the susceptibility of the bacteria to the agent is determined by comparing the color intensity of the stained, concentrated bacteria with a control. Differentiation of the gram-stain of bacteria may be effected by treating the stained bacteria with an organic acid wash having a pH of about 2.5–2.6. Gram-positive bacteria are completely decolorized by such a wash whereas stained gram-negative bacteria are not.

The composition and methods of the invention have particular application to the detection and analysis of bacteria in physiological fluid specimens, particularly urine specimens. By means of the instant invention, rapid and economical detection and treatment of bacterial infection is possible.

More particular, it has been discovered that the combination of a chelating agent, operative in the basic pH range, and a dye, capable of staining bacteria at a pH above about 7.0, results in a composition having the capacity to stain both gram-negative and gram-positive bacteria. In the absence of the chelating agent, dyes, particularly basic dyes, fail to stain gram-negative bacteria. Bacteria may be stained simply by contacting either concentrated or fluidly suspended bacteria with the chelating agent/dye composition at a nearly neutral or basic pH.

Any dye capable of staining bacteria at a basic or neutral pH may be employed in the composition and method for staining bacteria described herein. Since the staining operation is effected at a pH of about 7 or higher, the dyes used must be operative in this pH range. As a general rule, basic or cationic dyes are effective bacteria stains in the practice of the present invention. Specifically, Safranin-O, toluidine blue, methylene blue, crystal violet and neutral red may be utilized in the present invention, with Safranin-O being particularly preferred.

The chelating agents which may be employed in the practice of the present invention are also limited to those which are operative at the pH at which the staining is effected, that is, about 7.0 or higher. Salts of ethylenediaminetetraacetic acid (EDTA) and citric acid may be utilized. In particular various sodium salts of these two acids are effective, specifically the di- and tetrasodium salts of EDTA and the di- and trisodium salts of citric acid. Tetrasodium EDTA is a particularly preferred chelating agent.

The amounts of chelating agent and dye necessary to effectively stain bacteria range from about 0.001 to about 0.1 molar (M) chelating agent and 1:1000 to 1:300,000 dilution of dye. These amounts are calculated as final concentrations, taking into account any dilution due to the material in which the bacteria may be present.

The specific concentration of dye and chelating agent utilized may be dependent in part upon the condition of the bacteria when contacted with the staining composition. For example, where the staining is effected on bacteria which are relatively concentrated or free of interfering substances, competing chemical or physical reactions will as a rule be reduced and more concentrated compositions may be employed. On the other hand, where the bacteria are dispersed in a fluid medium containing other materials, it may become necessary to adjust the concentration of dye and/or chelating agent upward or downward to compensate for reactions with these additional materials. For example, in urine specimens, reduced concentrations of dye should be used to avoid formation of precipitates with urine compounds which occurs at 1:1000 dye dilution. In general, dye dilution on the order of 1:2500 or more is adequate to avoid such precipitate formation, but dilution of 1:10,000 or more is preferred. In general, particularly effective bacteria staining can be accomplished employing compositions comprising about 0.05 M chelating agent and 1:1000 or higher dye dilution with relatively pure or concentrated bacteria or 0.05 M chelating agent and 1:10,000 or higher dye dilution where the bacteria is fluidized with interfering materials.

In practice, the staining composition may be stored in concentrated form. For example, sterile Safranin-O EDTA could be stored at the following concentrations: Safranin, 1:1000; EDTA $Na_4$, 0.5 M. At the time of use, this mixture could be diluted to the desired concentration. For example, 1 ml could be added to 9 ml of test material to obtain a final concentration of 1:10,000 Safranin and 0.05 M EDTA. The storage stability of the staining composition is increased when the dye used to make the composition has been solubilized in undiluted organic media.

As indicated above, the composition is effective to stain both concentrated bacteria and fluidly suspended bacteria. Staining of bacteria is accomplished simply by adding the composition to a fluid specimen believed to contain bacteria or by contacting a solution of the composition with concentrated bacteria. Thus, for example, bacteria in physiological fluid specimens may be stained by simply adding the composition to the specimen. Alternatively, the bacteria might first be deposited on a semi-permeable membrane. Thereafter, staining of the bacteria could be effected by pouring a solution of the composition through the membrane.

The degree of staining is somewhat dependent upon concentration of dye and time of contact. With higher concentrations, the period of contact may be reduced; conversely with lower concentrations of dye, increased holding times are required. Further, the time of contact is inversely related to the temperature at which the contact is effected. For example, optimal staining of bacteria in fluid specimens with a dye dilution of 1:5000 requires holding times of 45 minutes at 4° C., 15 minutes at 25° C., 5 minutes at 37° C. and 1 to 2 minutes at 50° C. In general, at least 15 minutes at room temperature is required to obtain maximum staining of bacteria in urine specimens; after 30 minutes, no further staining is observed. However, if the bacteria is concentrated on semi-permeable membranes prior to staining, periods of as little as 15–60 seconds are required, since staining compositions having a 1:1000 dye dilution may be employed.

Bacteria stained in accordance with the present invention may be readily detected if concentrated. When the staining has been effected on concentrated bacteria in a manner which does not result in the bacteria becoming fluidized, the presence of bacteria is immediately manifested. Stained bacteria which are fluidly dispersed will, upon concentration, become readily visible.

The concentration of bacteria which can be detected by this staining procedure varies somewhat with the type of bacterium, but in general gram-negative bacteria can be detected at levels of $10^5$ CFU/ml, whereas detection of gram-positive bacteria may require accumulation of $10^6$ CFU/ml. Of course, smaller concentrations of bacteria can be detected by concentrating larger quantities of fluid.

Sedimentation and filtration are examples of effective means for concentrating bacteria. When sedimentation is employed, bacteria present in the specimen will be manifested by a precipitate having the color of the dye employed. With filtration techniques, bacteria are deposited on semi-permeable membranes whereupon their presence is evidenced by the color of the dye developing on the membrane.

Conventional procedures, such as centrifugation may be employed to effect sedimentation. For example, bacteria in a 100 ml physiological fluid specimen could be sedimented at 3000 rpm for 15–30 minutes in a conventional chemical centrifuge, after being contacted with the composition of the invention. A pellet in the tube having the color of the dye used indicates the presence of bacteria.

Where the present invention is practiced utilizing filtration techniques, a semi-permeable membrane having a pore size sufficient to retain bacteria is required. In general, membranes having a pore diameter of about 0.2 to 1.0 μm may be employed. The membrane may contain conventional materials, including fiberglass, epoxy, nitrocellulose, cellulose acetate, asbestos or combinations thereof. Preferred are epoxy-fiberglass filters having good flow rates and a depth such that clogging is minimized. Flow rates and depth of a membrane are of particular importance when dealing with very turbid specimens, such as urine.

Further, it is preferred that the membrane employed not retain substantial amounts of dye which are not associated with bacteria. Retention of free dye by the membrane is preferably sufficienty low to permit differentiating the color developed on the membrane when only free dye is present and that developed when stained bacteria is additionally present. In general, membranes which do not have a net negative electrostatic surface charge must be employed. The relative suitability of membranes can be evaluated by simply passing the appropriate concentration of the dye being used through the various membranes and comparing the intensity of color developed.

Preferred membranes are those which adsorb minimal amounts or no free dye. However, if the dye/membrane combination is such that free dye partially colors the membrane surface, the presence of stained bacteria can be accurately detected in accordance with the present invention simply by subtracting the intensity of this partial coloration as background. To insure accurate detection of bacteria, the color developed on the membrane during a control run utilizing a fluid specimen containing a staining composition, but no bacteria could be compared with the color developed in a run utilizing a similar specimen containing the staining composition and a pathological amount of bacteria.

Some membranes which are colorized by free dye can be decolorized partially or completely by means of an organic acid wash. By contacting organic acids with some membranes, the surfaces of which are colorized by the staining composition in the absence of bacteria, at least part of the free dye adsorbed by the membrane surface can be removed without removing dye associated with bacteria deposited on the membrane. Such an acid wash, thus, reduces the amount of free dye retained by some membranes and thereby improves the accuracy with which bacteria may be detected on such membranes.

The degree of decolorization effected by an acid wash will depend on a number of factors, including nature of the membrane, particular acid used, pH of the acid and material in which the dye is solubilized. The color developed due to free dye on membranes containing various materials, including fiberglass, nitrocellulose, cellulose acetate, asbestos and epoxy, may generally be removed to some degree by an organic acid wash. Organic acids, including citric and acetic acid, are generally effective to remove free dye on membrane surfaces, without removal of dye attached to bacteria, if the pH of the acid is between about 2.7 and 4.0. pH's below about 2.7 should be avoided since decolorization of stained bacteria may also occur. Acetic acid at a pH of about 3 is a preferred wash.

The degree of attachment of free dye to membranes can be reduced and removal thereof by an acid wash can be enhanced if the dye utilized in the staining composition is solubilized in organic media. Basic dyes dissolved in water or inorganic salts tend to attach to membranes and are not generally decolorized by an organic acid wash.

Most effective removal of free dye is accomplished in those cases where a basic dye has been completely solubilized in rich organic media. The degree of solubilization may be determined by passing a test solution of the basic dye through a cation exchange resin and thereafter filtering the eluent through a membrane having a capacity to adsorb the dye. The degree of solubilization will be indicated by the amount of dye adsorbed on the membrane; where a dye is completely solubilized, no dye will be evident on the membrane, whereas relatively lesser degrees of solubilization will be indicated by the relatively increased intensity of the color developed on the membrane.

Solubilization of basic dyes can be accomplished in rich organic media used for culturing bacteria, such as trypticase soy broth, tryptose phosphate broth, glucose or brain-heart infusion. Preferred media include undiluted trypticase soy broth, tryptose phosphate broth, brain-heart infusion or media of similar nature, since not only do such media minimize the incidence of false positives, but additionally result in staining compositions which exhibit a reduced tendency to precipitate or become turbid over time and thus are more storage stable.

A preferred combination for maximizing removal of free dye adsorbed by membrane surfaces is as follows: a fiberglass-epoxy filter having a net positive surface charge and particularly one having the pore and flow properties of the G-2 series sold by Finite Filter Corp. (Detroit, Mich.), acetic acid at a pH of about 3 and a basic dye, preferably Safranin-O, solubilized in undiluted bacteria culturing media. Substantially all free dye on a membrane surface is decolorized when this combination is employed in the practice of the present invention.

The decolorizing acid wash may be effected simply by contacting the colored surface of the membrane with the acid for a short period and thereafter suctioning or otherwise removing the wash from the membrane. The optimum time and number of washes can be determined by simple trial and error control runs. Typically, with an acid at pH 3, 1 to 3 washes for a period of less than five minutes each will be sufficient.

The presence of bacteria can be semi-quantitatively detected employing the staining composition of the invention. Such a quantitative analysis can be accomplished by simply staining and concentrating the bacteria as above described.

The intensity of the color of the stained, concentrated bacteria, which correlates with the bacterial population, can then be compared with a standard which has been calibrated using known bacterial amounts. Conventional techniques, such as nomographic, colorimetric and photometric procedures, may be employed to make the quantitative analysis. Bacterial growth in fluids may be measured using the above methodology by comparing the intensity of bacterial stains developed in samples drawn from the fluid at different time intervals.

Differentiation of the gram-stain of bacteria may also be accomplished employing the staining composition of this invention. As noted above, organic acid washes below a pH of about 2.7 tend to decolorize stained bacteria as well as free dye on a membrane surface. However, if the pH of the acid is maintained at about 2.5 to 2.6, gram-positive bacteria are totally decolorized; below a pH of about 2.5 both gram-positive and gram-negative bacteria are decolorized. It is thus possible to differentiate gram-negative and gram-positive bacteria. Thus, by means of an organic acid wash, of the type used to decolorize free dye on a membrane, but having a pH reduced to about 2.5 to 2.6, a semi-qualitative analysis of bacteria stained with the composition of the invention can be performed.

By means of the present invention, it is also possible to determine antimicrobial susceptibilities of bacteria. Treatment of bacteria with an antimicrobial agent to which they are susceptible prior to contact with the staining composition will result in a diminution in number of bacteria. Consequently, the color of the stained concentrated bacteria thus treated will be less intense than that of resistant cultures or an untreated control. The reduction in color will be roughly parallel to the degree of susceptibility to the antimicrobial agent. Thus, when bacteria are treated with an antimicrobial agent prior to contact with the staining composition of the invention, the intensity of the color of the stained, concentrated bacteria will be related to the susceptibility of the bacteria to the agent. Treatment of bacteria with an antimicrobial agent having a bacteriostatic or bactericidal effect prior to staining will result in the color intensity of the stained concentrated bacteria being comparatively less than that of stained concentrated bacteria which were not treated with the agent. By comparing the colors developed in bacteria which have been treated with different antimicrobial agents or different amounts of a single agent, the relative inhibitory effects thereof can be evaluated.

Treatment of bacteria with an antimicrobial agent can be effected simply by contacting either concentrated or fluidly suspended bacteria with the agent generally for no more than about 1 to 3 hours. The procedure may be employed with bacteria in a fluid specimen or with colonies of bacteria from a culture plate which have been suspended in an organic broth. The amount of agent employed in this procedure will be in accordance with known standards, such as standardized FDA approved antimicrobial discs.

If desired, a bacteria sample may be incubated prior to treatment with antimicrobial agents. Incubation will enhance the accuracy with which susceptibility to the agents is determined due to the culture reaching log phase of growth. Since bacteria grow at a rapid rate when incubated at 35°-36° C., bacterially infected samples need be incubated for only about 30 minutes to 1 hour to insure highly accurate results. Such incubation is desirable where the relative inhibitory effects of several antimicrobial agents having similar activities are being assessed.

The composition and methods of the invention have particular application to the staining and analysis of bacteria in physiological fluid specimens. For example, urine, which has been clarified conventionally, may be treated with a solution containing 1:10,000 Safranin-O solubilized in nutrient broth and 0.05 M tetrasodium ethylenediaminetetraacetate. The urine is then passed throgh a bacteriological filter having a net positive charge whereupon the stained bacteria are readily visible. If desired, the filter is then washed with pH 3 acetic or citric acid.

Alternatively, the urine may be passed through the bacteriological membrane which results in the deposition of the bacteria in the urine onto the membrane surface. Thereafter, the deposited bacteria are treated with sufficient 1:1000 basic dye—0.05 M EDTA salt mixture to cover the membrane surface. After 15-60 seconds, or longer if desired, the dye is drawn through the membrane by suction. If desired, the membrane may then be washed with pH 3 acetic acid.

In some instances, urine of patients suffering with bacteriuria may have precipitates which clog membranes used in the practice of the present invention. Such urine is first clarified, for example with a 5 $\mu m$ clarifier, to remove the precipitates and enhance filtration of the urine. Occasionally, urine may contain gram-positive bacteria in the form of aggregates which are removed by the 5-$\mu m$ clarifier. Without clarification, such urines would not be able to be processed by the bacteriuria-detection method of the invention.

In order to increase the flow rates of urine through the 0.65-$\mu m$ filters employed in the present method, the sediments, such as urates, present in the urine may be solubilized. Acetic acid is the optimal solvent for this purpose. Urine specimens mixed with equal volumes of acetic acid at pH levels of 2.0, 2.5, 3.0, 3.5 and 4.0 exhibit increased optical transmission at 540 nm only at pH 2.5 or lower. Further, mixtures of pH 2.5 acetic acid and urine attain a final pH between 3.5 and 4.5 in most cases and are not deleterious to the staining reaction of bacteria (i.e., the bacteria retained their ability to react with safranin).

The acetic acid diluent enhances the flow rates of urines. In many instances, the staining intensity is greater in the acetic acid diluted urines than in corresponding specimens without acetic acid. This is believed to be due to the fact that suspended solids which are solubilized can no longer impact on the entrapped bacteria on the filter and prevent staining.

Although the acetic acid diluent described above aids flow rates of urines which contain solids, heavily pigmented urines containing soluble organics often clog membranes because of the adsorption of the pigments to the 0.65-μm filters. Among anionic exchangers which remove urine pigments, Exchanger A109-D (Diamond Shamrock, Cl⁻ charged) is the resin of choice since it renders the urine almost colorless. Flow rates of urines through 0.65-μm filters are dramatically increased if the urine is first passed through the anionic resin. Urines may be processed employing such a resin as follows: 3 ml of a urine specimen is passed through 5-gram resin column resulting in recovery of 2.5 ml of the specimen in the resin filtrate. This filtrate is then mixed with an equal volume of acetic acid diluent and processed through the filter, stained and washed as previously described.

Resin treatment in this manner enhances rapid filtration of the sample through filters. The average flow rate of such samples is 0.2 minutes. Also, some positive bacteriuria samples which may appear negative without resin treatment, will produce positive results when the resin is used. Additionally, urines which clog filters without resin treatment will pass them more easily after the resin treatment.

Incorporation of the resin treatment into the method of the invention may be accomplished as follows: Elkay filters (serum separators), which are 10-ml plastic tubes with filters (30-40 μm) at the butt of the tube and a skirt protruding around the butt which forms a seal when the separator, are loaded with 5 grams of resin suspended in water containing 1:250 formalin and are placed in 16-mm test tubes each of which contains 2.5 ml of pH 2.5 acetic acid. The fluid phase of the resin suspension is then drawn off by vacuum, leaving a moist resin column within the separator. The residual formalin maintains the sterility of the column. The separator is then placed in the 16-mm tube containing the acetic acid by forcing the butt of the Elkay tube into the 16-mm tube and driving the plastic tube into the acetic acid. Tubes may be thus prepared prior to use and stored in this manner. At the time of use, 3.0 ml of urine is added to the Elkay tube (which has about 4.5 ml of reservoir volume above the resin column). The Elkay tube is then gripped and removed slowly from the test tube. This action produces a vacuum in the test tube because the Elkay skirt against the sides of the tube, thus drawing the urine through the resin and into the acetic acid. The end result is a 5-ml sample containing the urine and acetic acid, which may then be filtered, stained and washed in accordance with the method of the invention.

Although the acetic acid diluent and the resin exchanger increase the efficiency of the bacteriuria-detection method, there are still occasional urines which give problems due to the presence of pigments that are not removed by the anionic resin exchanger. Blood, hemoglobin, certain basic drugs, and basic pigments present in urine of patients with certain pathologic disorders will coat the 0.65-μm filter and prevent staining of the bacteria. For example, when urine containing blood is processed, the erythrocytes pass the resin (since cells cannot exchange with resin). When mixed with acetic acid, the blood cells are lysed and the basic hemoglobin is concentrated onto the filter in the form of a greenish pigment, which interferes with the staining of bacteria. However, when such filters are treated with hydrogen peroxide, the problem is resolved. A 30-second treatment of a filter containing hemoglobin with 0.2 ml of 30% $H_2O_2$ completely clears the filter of color. Staining of the filter with safranin-EDTA and subsequent washing indicate that the peroxide has no effect on the stainability of the bacteria. In fact, peroxide treatment of bacteria often enhances the staining. Therefore, in all cases where filters manifest excess pigment (after processing through the resin and acetic acid) on 0.65-μm filters, they may be treated with $H_2O_2$ as described above for 30 seconds. Thereafter they are stained and washed as described earlier in this application.

Occasionally, very turbid, bloody or dark amber urines will deposit a precipitate or pigmented compound on the membrane. Staining of this material may lead to false-positive results. In those cases where urine samples are so heavily contaminated with precipitates, such as phosphates, carbonates, urates or blood, it may be possible to employ the methods of the present invention if the specimen is centrifuged at low speeds whereby these materials are sedimented without sedimentation of bacteria. Centrifugation at speeds on the order of 500 rpm are generally effective for this purpose. As a result of such centrifugation, the bacteria-containing supernatant will more readily pass through the filter. This procedure will reduce false-positives and will uncover positives that may be masked by the excess pigment deposits.

The composition and methods described herein may similarly be applied to the staining, detection and analysis of gram-negative and gram-positive bacteria in other fluids, such as culture media, blood, spinal fluids and water, as well as to staining bacteria from such fluids which have been deposited on membranes.

The following examples are illustrative of the invention and are not to be taken in a limiting sense.

EXAMPLE 1

To a 100-ml sample of normal, bacteria-free urine was added *E. coli* (gram-negative bacteria) to make a final concentration of $10^6$ colony-forming units (CFU)/ml. *Staphylococcus aureus* (gram-positive bacteria) was added in a similar manner to a second urine sample. The urine was then treated with Safranin-O (a red, basic dye) at a dilution of 1:200,000. A control sample of urine without added bacteria was also treated with the dye as described.

The samples were held at room temperature (RT) for 30 minutes and then tubes containing the 100-ml urine samples were centrifuged at 3000 rpm for 30 minutes. The tubes were then inspected for stained bacteria. The tube containing the added *E. coli* manifested a pellet at the bottom of the tube, but no red color was evident, only the typical grayish mass seen when unstained bacteria are pelleted. In the tube containing the *Staphylococcus aureus* was a pellet having a red color. The control tube contained no pelleted mass.

The experiment was repeated with crystal violet and toluidine blue. In both cases, the pellet deposited in the *E. coli* tube was not colored, while in the *Staphylococcus aureus*-containing tube the pellet exhibited the color of the dye used: dark blue with the toluidine blue and purple-blue with crystal violet.

EXAMPLE 2

100-ml samples of normal pooled urine were treated with $10^6$ CFU/ml *E. coli* and 1:200,000 Safranin-O. The control samples were treated with the dye but were not treated with bacteria. All samples were treated with the tetrasodium salt of EDTA concentrations indicated below. The samples were held at RT for 30 minutes, and the 100-ml tubes were then centrifuged at 3000 rpm for 30 minutes to sediment the bacteria.

The bacteria pellet at the bottom of each tube was scored for the amount of Safranin present in the pellet. O=no color to the pelleted bacteria. ±=trace of red. +, ++, +++, ++++ indicate increasing amounts of dye attached to the bacteria. In addition, the supernatant fluids after centrifugation were tested for absorbance at the wavelength of the dye (520 nm) to determine the percentage of dye removed by bacteria. The results were as follows:

TABLE 1

| Final conc. EDTA in urine (m) | E. coli containing urine | | | Control urine | | |
|---|---|---|---|---|---|---|
| | Pellet | Absorbance | % removed | Pellet | Absorbance | % removed |
| none | 0 | .423 | 0 | 0 | .420 | 0 |
| 0.01 | ± | .390 | 6 | 0 | .415 | 0 |
| 0.02 | + | .320 | 23 | 0 | .424 | 0 |
| 0.03 | ++ | .280 | 33 | 0 | .409 | 0 |
| 0.04 | ++++ | .190 | 54 | 0 | .416 | 0 |
| 0.05 | ++++ | .185 | 56 | 0 | .421 | 0 |
| 0.06 | ++++ | .196 | 53 | 0 | .409 | 0 |
| 0.07 | ++++ | .199 | 52 | 0 | .424 | 0 |

The results in Table 1 indicate that, in the presence of EDTA, significant amounts of dye become attached to the bacteria and are found in the pellet.

Essentially the same results were obtained upon repetition of the above experiment with the following basic dyes: crystal violet, toluidine blue, methylene blue and neutral red.

EXAMPLE 3

Employing the procedure set forth in Example 2, experiments were conducted with a variety of organisms using Safranin-O as a model dye. The results were as follows:

TABLE 2

| Test organism | Gram stain | Dye attachment | |
|---|---|---|---|
| | | No EDTA | 0.05 M EDTA |
| E. coli | − | 0 | +++ |
| S. aureus | + | ++++ | +++ |
| Proteus vulgaris | − | 0 | ++++ |
| Pseudomonas | − | 0 | ++++ |
| Group A Strep. | + | ++++ | +++ |
| Group D Strep. | + | ++++ | +++ |
| Klebsiella pn. | − | 0 | ++++ |

The results indicate that gram-negative organisms require the presence of a chelating agent to bind the basic dye to bacteria in urine, whereas gram-positive bacteria are stained by the dye both in the presence and absence of a chelating agent.

Further experiments revealed that 1:5000 basic dye was more effective in producing stained pellets in urine than the dye in dilute form, as described above (i.e., 1:200,000). Even with the higher concentration of dye, EDTA was still required for dye-attachment to gram-negative organisms.

EXAMPLE 4

1:500 suspensions of Safranin-O were made in the diluents indicated below. The samples were then autoclaved at 15 psi for 30 min. After cooling, the autoclaved samples were filtered through a 0.22-μm Millipore filter. The filtrate was then mixed with an equal volume of 0.1 M EDTA to attain a final of 1:1000 Safranin and 0.05 M EDTA.

Ten-ml samples of normal urine were then passed through 13-mm diameter, 0.65-μm porosity fiberglass-epoxy Finite filters. The dye-EDTA stocks indicated below were used to treat the membranes through which the urine had passed, by holding the stocks in contact with the membranes for a 1-min staining period. Thereafter, the stain was suctioned through the membrane. The membrane was then washed twice with 5 ml of pH 3 acetic acid to decolorize the membrane.

The membranes were then scored as follows: 0, complete decolorization of membrane, which appears white; +, faint tinge of red; +, definite red coating of membrane; ++, red to purple color. All scoring other than "0" represents false positives. In addition, the turbidity of the dye stocks was scored with 0 indicating no turbidity and +, ++, +++ and ++++ indicating increasing turbidity. The dyes were then stored at ambient temperature, and the quality of the suspension was similarly scored after 24 hours.

The results of these tests are set forth in Table 3.

TABLE 3

| Diluent for dye | Membrane score | Turbidity of dye-EDTA stocks at | |
|---|---|---|---|
| | | 0 hr | 24 hr |
| Distilled water | + | +++ | ++++ |
| Saline | + | ++ | ++++ |
| Trypticase soy broth (undiluted) | 0 | 0 | 0 |
| 1:10 broth in water | + | 0 | + |
| 1:100 broth in water | + | 0 | ++ |
| Tryptose phosphate broth | 0 | 0 | 0 |
| 1:10 broth in water | + | 0 | + |
| 1:100 broth in water | + | 0 | +++ |
| Trypticase soy broth 1:10 in saline | + | 0 | + |
| Tryptose phosphate broth, 1:10 in saline | + | 0 | + |
| 5% glucose in water | 0 | 0 | ++++ |
| 10% calf serum in water | + | 0 | ++++ |
| 1% sodium acetate | ++ | 0 | (not done) |

The results in Table 3 indicate that only undiluted tryptose phosphate broth, trypticase soy broth and glucose yielded a dye product that could be completely removed from the membrane with the acid wash. All other diluents, including dilutions of broths in water or saline, resulted in some degree of staining of the membrane. Further, after overnight storage, all dye-EDTA mixtures, except those in undiluted broths, had at least begun to precipitate.

EXAMPLE 5

Ten-ml urine samples were treated with 0.05 M EDTA and 1:10,000 Safranin-O in trypticase soy broth and were held at RT for 30 minutes. Samples were then passed through 13-mm, 0.65-μm bacteriological membranes (epoxy-fiberglass). The membrane was then washed with 5 ml of the acids indicated below. The membranes were then scored with 0 indicating no color on the membrane and +,++, +++, ++++ indicating increasing membrane color. The results were as follows:

TABLE 4

| Washing agent | Normal Urine (no bacteria) | |
|---|---|---|
| | Color before wash | Color after wash |
| pH 3 acetic acid | ++ | 0 |
| pH 3 citric acid | ++ | 0 |
| pH 3 HCl | ++ | ++ |
| pH 3 H$_2$SO$_4$ | ++ | + |
| pH 3 nitric acid | ++ | ++ |

Similar tests were run on samples to which bacteria were added using pH 3 acetic acid. The results of these tests, scored as in Table 4, are set forth in Table 5.

TABLE 5

| Test bacteria added to urine | Urine + Bacteria | |
|---|---|---|
| | Color before wash | Color after wash |
| E. coli | ++++ | ++++ |
| S. aureus | +++ | +++ |
| Pseudomonas | ++ | ++ |
| Group A Strep. | ++++ | ++++ |

The results of these experiments indicate that dye attached to bacteria is not removed by an organic acid wash, whereas free dye adsorbed by the membrane is removed by such a wash.

EXAMPLE 6

A patient's urine may be tested for bacteriuria at a pathognomonic level (i.e., bacteria in urine at levels of 10$^5$ CFU/ml or greater) as follows. To a 9-ml sample of the urine 1 ml of a ten fold Safranin-O/EDTA concentrate is added, mixed and held at 25° C. for 30 minutes and then placed in a vessel, which is connected in series to a 25-mm diameter clarifying 5-μm polypropylene felt filter and a 13-mm diameter bacteria-retaining 0.65-μm white fiberglass-epoxy filter which can be decolorized by pH 3 acetic acid. The urine is passed through the polypropylene filter and then through the bacteria-retaining filter by negative pressure. After the total sample passes the filters, the filters are treated with 5 ml of pH 3 acetic acid—1:500 formalin mixture by passing this fluid through both filters under negative pressure. The 13-mm fiberglass-epoxy filter is then examined for color. The color of the membrane is matched with a nomograph which indicates the expected bacterial counts based on color intensity of the membranes.

In an actual clinical trial using the above procedure, the patient's treated urine rendered the membrane surface orange-red, indicating approximately 10$^7$ CFU/ml bacteria.

EXAMPLE 7

To determine whether or not a patient has responded favorably to an antibiotic, the procedure outlined in Example 6 may be repeated at intervals. Antiobiotic effectiveness is indicated if no bacteria are evident or the intensity of the color is reduced, following commencement of antibiotic therapy. On the other hand, the same or increased intensity indicates bacterial resistance to the antibiotic administered.

The patient described in Example 6 was placed on Keflin (a penicillin-type antibiotic). The following day, his urine was re-examined as described in Example 6. The results were again positive, showing an orange-red color that indicated about 10$^7$ CFU/ml bacteria and indicating that the organism was resistant to the Keflin antiobiotic. Gentamycin was then prescribed and upon testing the patient's urine the next day, the filter surface manifested an off-white color, indicating absence or very low level bacteria and that the antibiotic most recently prescribed was effective.

EXAMPLE 8

As an alternative to the method described in Example 6, a patient's urine may be tested for bacteriuria at a pathogenic level as follows: 10 ml sample of urine is passed through a bacteriological, 13-mm diameter, 0.65 μm fiberglass-epoxy filter described in Example 6 to deposit bacteria present in the urine thereon. The membrane is then treated with a 0.5 ml of a 1:1000 Safranin-O-0.05 M EDTA mixture for 30 seconds to 1 minute. The dye is then drawn through the membrane by suction and the membrane is washed with 3–5 ml portions of acetic acid as described in Example 6. One portion may be removed through a side drain to remove excess dye and the others may be removed through the filter. The color of the membrane may then be matched against a nomograph to determine the degree of bacteriuria.

EXAMPLE 9

Septicemia or bacteremia can be detected as follows: a blood culture is made by diluting a blood sample tenfold with culture broth. The sample is incubated at 36° C. Every hour (starting 3 hours after the initial incubation period at 36° C.) a 3-ml sample is removed from the blood culture. The sample is passed through a 2-μm clarifying membrane to remove blood cells and debris. The filtrate is then treated with dye and EDTA as described in Example 6, except that only 0.3 ml of the dye-EDTA test solution is added to the 3-ml sample. The sample is held at 25° C. for 30 minutes and then passed serially through the clarifier and fiberglass-epoxy filter as in Example 6. After a 5-ml acetic acid-formalin wash, the filter is observed for color and compared with a nomograph.

Results of such a test using a patient's blood are shown below.

TABLE 6

| Hours after culture initiated | Color of membrane | Scoring for bacterial growth* |
|---|---|---|
| 3 | white | 0 |
| 4 | faint pink | ± |
| 5 | orange | + |
| 6 | orange-red | ++ |
| 7 | dark red | ++++ |

*Scoring as in Example 5

These results indicate that using the method of the present invention, after only a 4–5 hour incubation period, it was possible to determine that at least 10$^5$ CFU/ml bacteria were present in the culture. This is a far shorter period than that which would be required to produce turbidity even in clear (blood-free) fluid systems, which normally would appear only after 24 hours.

EXAMPLE 10

5 ml of spinal fluid from a patient suffering from septic meningitis was added to 50 ml of culture broth and incubated at 36° C. At the intervals indicated below, 3-ml samples were obtained from the culture and processed as described in Example 9. At these same intervals, the culture was observed for gross turbidity, which would indicate bacterial growth. The results are shown below.

TABLE 7

| Hours after culture initiated | Visual turbidity of culture | Color of membrane | Scoring for bacterial growth |
|---|---|---|---|
| 3 | 0 | white | 0 |
| 4 | 0 | pinkish-orange | ± |
| 5 | 0 | orange | + |
| 6 | 0 | orange-red | ++ |
| 7 | + | red | +++ |
| 8 | + | dark red | ++++ |

The presence of bacteria was manifested using the method of the invention 3 hours before turbidity had become evident in the culture media. This is a significant advantage when a patient is suffering with a serious disease such as meningitis.

EXAMPLE 11

Antimicrobial susceptibility of bacteria may be determined as follows: A rich organic broth suspension of bacteria is diluted and divided into aliquots—one for each antibiotic to be tested plus a control—and placed in wells in a cuvette in contact with an antimicrobial elution disk. A zero hour control is made by adding formalin to the original inoculum and incubating and reading under the same conditions as the test. The cuvettes are agitated briefly by rotary motion at 200 rpm in a 36° C. incubator and then incubated until several generations of growth occur, i.e., 1½ to 3 hours. The cultures are then stained and filtered as described in Example 6. The intensity of the color of each antimicrobial-containing culture is compared with the control. Resistant cultures exhibit the same color intensity as the control, while susceptible cultures show less color and intermediate cultures fall in-between.

EXAMPLE 12

Levels of antibiotics in blood may be determined as follows: A patient's blood is obtained and the serum removed. The serum is twofold serially diluted in culture media. 1 ml samples of the different serum dilutions are placed in tubes and then each is treated with a 0.1 ml suspension of the original bacteria isolated from the patient ($\sim 10^5$ CFU/ml). The tubes are then incubated at 36° C. for 2–3 hours.

A second set of tubes are run side by side with the ones described above. In the second set of tubes are placed 1 ml samples containing a range of known concentrations of the antibiotic which is present in the patient's blood. Each serially diluted antibiotic sample is then treated with a 0.1 ml bacterial suspension and incubated as described above.

A control is prepared by placing a 1 ml sample containing no antibiotic in a tube, treating it with 0.1 ml bacteria suspension and incubating as above.

At the end of the 2–3 hours incubation period, each sample is stained, filtered and washed as described in Example 8. The colors of the membranes are scored to determine the most dilute serum sample and the least concentrated antibiotic sample (i.e. MIC) which have an inhibitory effect on bacterial growth, (i.e., the least concentrated serum which has comparatively less color intensity relative to the control and the lowest concentration of antibiotic which exhibits a less intense color than the control, respectively). Multiplication of this degree of dilution level by the minimum inhibitory concentration gives the concentration of the antibiotic in the patient's blood.

EXAMPLE 13

Several urines known to be positive for bacteriuria (based on plating and counting colonies) but which were difficult to process through the bacteriuria-detection device because of suspended solids being present, were treated with an equal volume of pH 2.5 acetic acid—0.05 M glycine diluent. Duplicate urine samples were mixed with an equal volume of sterile water as controls. In each case the total sample (in this case 2.5 ml urine+2.5 ml acetic acid or 2.5 ml sterile water) was filtered through a 10-mm diameter, 0.65-μm filter and the flow rate recorded. The filters were then stained and washed with pH 3 acetic acid as described above and color intensities of membranes scored accordingly. The results are shown below:

| Patient no. | Causative agent | CFU/ml | Color intensity of filter/flow rate Urine + water | Color intensity of filter/flow rate Urine + acetic acid |
|---|---|---|---|---|
| 10 | Proteus | $10^6$ | clogged | +/1.7 |
| 11 | E. coli | $10^6$ | +/1.9 | ++/0.9 |
| 12 | E. coli | $3 \times 10^5$ | clogged | +/1.4 |
| 13 | Pseudomonas | $5 \times 10^5$ | clogged | +/1.6 |
| 14 | S. aureus | $3 \times 10^5$ | 0/1.8 | +/0.7 |
| 15 | Enterococci | $6 \times 10^5$ | clogged | 0/1.7 |
| 16 | Enterococci | $2 \times 10^5$ | 0/1.9 | ±/0.9 |
| 17 | S. epidermidis | $8 \times 10^5$ | 0/1.9 | 0/1.4 |
| 18 | K. pneumoniae | $10^6$ | +/2.0 | ++/0.9 |
| 19 | S. marcescens | $10^6$ | ±/1.8 | +/0.8 |

*Numerator indicates color intensity of filter surface. Denominator indicates the time in minutes to filter the total sample.

EXAMPLE 14

A urine sample which contained excess precipitates and which was heavily pigmented was processed using the acetic acid diluent method described in Example 13. The urine, although free of visual precipitates, still clogged the membrane and the test could not be completed. However, the test was repeated by passing 3 ml of urine through a 5-gram anionic resin column (A109-D, Diamond Shamrock, Cl$^-$ charged), and 2.5 ml of the filtrate was collected in 2.5 ml of acetic acid diluent. The 5-ml sample was then passed through the 0.65-μm filter, which only required 0.2 minute. After staining and washing with pH 3 acetic acid as described above, the resultant filter surface manifested a red color indicating bacteriuria.

When another urine was processed, which was known from plating to be negative for bacteriuria, it clogged the filter when the acetic acid diluent only was used. When processed through the resin and collected in the acetic acid diluent as described above, and then stained and washed, the membrane manifested a typical off-white color indicative of a negative result.

Thus, the combination of the pH 2.5 acetic acid diluent and the resin exchanger resolves clogging problems and will allow the technician to make an immediate determination as to positive or negative bacteriuria, rather than having to wait for the 24–48 hours required if the sample had to be plated and examined for growth of colonies.

EXAMPLE 15

A bloody urine was passed through the anionic resin described in Example 14 and 2.5 ml of the resin filtrate was collected in 2.5 ml of pH 2.5 acetic acid diluent.

The total 5 ml was then passed through the 10-mm diameter, 0.65-μm filter and a greenish pigment coated the membrane. Staining of the filter with safranin-EDTA and pH 3 wash resulted in a bright green filter surface. The urine sample was then processed again as described above except the filter was first treated with 0.2 ml of 30% hydrogen peroxide for 30 seconds prior to staining. After the 30-second peroxide treatment, the peroxide was drawn through the filter and then stain was applied and the filter was washed with pH 3 acetic acid. The results indicated a strong positive bacteriuria, since the membrane surface now manifested a red color. Plating of the sample proved the urine to contain E. coli in an amount of $10^6$ CFU/ml.

Another bloody urine was processed as described above, but without peroxide treatment. Because of the pigments, it was impossible to determine whether bacteria were present. After treatment of the greenish filter surface with $H_2O_2$ as above, there was no pigment on the membrane. Staining and then washing with acetic acid resulted in a typical off-white color indicating a negative test. Plating failed to detect any bacteria.

Another sample of urine containing a fluorescent yellow pigment manifested a yellow filter surface. The resin had failed to remove this pigment, and staining with dye yielded a strong yellow color on the filter surface. $H_2O_2$ treatment removed the pigment, and the standard treatment now yielded a positive red color test for bacteria, which was later confirmed by plating.

What is claimed is:

1. A composition for staining bacteria at a pH above about 7.0 comprising:
    (a) a chelating agent effective at a pH above about 7.0; and
    (b) a dye capable of staining bacteria at a pH above about 7.0.

2. The composition of claim 1 wherein the chelating agent is a salt of ethylenediaminetetraacetic acid.

3. The composition of claim 2 wherein the chelating agent is a sodium salt of ethylenediaminetetraacetic acid.

4. The composition of claim 2 wherein the chelating agent is the tetrasodium salt of ethylenediaminetetraacetic acid.

5. The composition of claim 1 wherein the chelating agent is a salt of citric acid.

6. The composition of claim 1 wherein the dye is a basic dye.

7. The composition of claim 1 wherein the dye is selected from the group consisting of Safranin-O, toluidine blue, methylene blue, crystal violet and neutral red.

8. The composition of claim 1 wherein the dye is Safranin-O.

9. The composition of claim 1 comprising 0.001 to 0.1 molar tetrasodiumethylenediaminetetraacetate and 1:1000 to 1:300,000 dilution of Safranin-O.

10. The composition of claim 1 wherein the dye is solubilized in organic media.

11. The composition of claim 10 wherein the media is bacterial culture media.

12. A method of staining bacteria which comprises contacting the bacteria at a pH at or above about 7.0 with a composition comprising a chelating agent operative at a basic pH and a dye capable of staining bacteria at a basic pH.

13. A method of claim 12 wherein the chelating agent is a salt of ethylenediaminetetraacetic acid.

14. The method of claim 13 wherein the salt is the tetrasodium salt.

15. The method of claim 12 wherein the dye is a basic dye.

16. The method of claim 12 wherein the dye is Safranin-O.

17. The method of claim 12 wherein the step of contacting the bacteria is carried out in a fluid specimen.

18. The method of claim 17 wherein the fluid specimen is urine.

19. The method of claim 12 wherein the step of contacting the bacteria is carried out on a semi-permeable membrane which has a pore size sufficient to retain bacteria and does not retain substantial amounts of the free dye.

20. A method for detecting bacteria in fluids comprising:
    (a) staining the bacteria with a composition comprising a chelating agent operative above a pH of about 7.0 and a dye capable of staining bacteria at a pH above about 7.0; and
    (b) concentrating the bacteria, whereby dye associated with the bacteria is readily visible.

21. The method of claim 20 wherein the chelating agent is a salt of ethylenediaminetetraacetic acid.

22. The method of claim 21 wherein the salt is the tetrasodium salt.

23. The method of claim 20 wherein the dye is a basic dye.

24. The method of claim 20 wherein the dye is Safranin-O.

25. The method of claim 20 wherein the step of concentrating the bacteria is carried out by centrifugation.

26. The method of claim 20 wherein the step of concentrating the bacteria is carried out by depositing the bacteria on a semi-permeable membrane which has an average pore diameter of about 0.2 to about 1.0 μm and does not adsorb substantial amounts of free dye.

27. The method of claim 26 wherein the membrane is an epoxy-fiberglass filter having a net positive surface charge.

28. The method of claim 26 wherein the dye is solubilized in organic media.

29. The method of claim 28 wherein the dye is solubilized in bacteria culture media.

30. The method of claim 28 which further comprises washing the membrane with an organic acid having a pH between about 2.7 and 4.0 after the stained bacteria are deposited thereon.

31. The method of claim 30 wherein the organic acid is acetic acid.

32. The method of claim 26 which further comprises washing the membrane with an organic acid having a pH between about 2.5 to 2.6.

33. The method of claim 32 wherein the acid is acetic acid.

34. A method for quantitatively detecting the presence of bacteria in a fluid specimen which comprises:
    (a) staining the bacteria with a composition comprising a chelating agent operative at a pH above about 7.0 and a dye effective to stain bacteria above a pH of about 7.0;
    (b) concentrating the bacteria; and
    (c) thereafter comparing the intensity of the color of the bacteria with a known standard.

35. A method for differentiating gram-negative and gram-positive bacteria which comprises:

(a) staining the bacteria with a composition comprising a chelating agent operative at a pH above about 7.0 and a dye effective to stain bacteria above a pH of about 7.0;
(b) depositing the bacteria on a semi-permeable membrane which has a pore size sufficient to retain bacteria and does not absorb substantial amounts of free dye;
(c) thereafter washing the membrane with an organic acid wash having a pH between about 2.5 and 2.6; and
(d) thereafter observing the surface of the membrane to determine whether it has been decolorized by the acid wash of step (c).

36. A method for determining the susceptibility of bacteria to antimicrobial agents which comprises:
(a) treating bacteria with an antimicrobial agent;
(b) after the bacteria has been treated with the antimicrobial agent, staining the bacteria with a composition comprising a chelating agent operative at a pH above about 7.0 and a dye effective to stain bacteria at a pH above about 7.0;
(c) concentrating the bacteria; and
(d) thereafter determining the relative intensity of the color of the stained concentrated bacteria to determine the relative effectiveness of the antimicrobial agent.

37. The method of claim 36 wherein the chelating agent is a salt of ethylenediaminetetraacetic acid.

38. The method of claim 37 wherein the salt is the tetrasodium salt.

39. The method of claim 36 wherein the dye is a basic dye.

40. The method of claim 37 wherein the dye is Safranin-O.

41. The method of claim 36 wherein the step of concentrating the bacteria is carried out by centrifugation.

42. The method of claim 36 wherein the step of concentrating the bacteria is carried out by depositing the bacteria on a semi-permeable membrane which has an average pore diameter of about 0.2 to about 1.0 μm and does not adsorb substantial amounts of free dye.

43. The method of claim 42 wherein the membrane is an epoxy-fiberglass filter having a net positive surface charge.

44. The method of claim 42 wherein the dye is solubilized in organic media.

45. The method of claim 44 wherein the dye is solubilized in bacteria culture media.

46. The method of claim 44 which further comprises washing the membrane with an organic acid having a pH between about 2.7 and 4.0 after the stained bacteria are deposited thereon.

47. The method of claim 46 wherein the organic acid is acetic acid.

48. The method of claim 42 which further comprises washing the membrane with an organic acid having a pH between about 2.5 to 2.6.

49. The method of claim 48 wherein the acid is acetic acid.

50. A combination for detecting bacteria in fluids comprising:
(a) a chelating agent effective at a pH above about 7.0;
(b) a dye capable of staining bacteria at a pH above about 7.0; and
(c) a semi-permeable membrane which has an average pore diameter of about 0.2 to about 1.0 um and does not adsorb substantial amounts of free dye and on which the bacteria can be concentrated.

51. The combination of claim 50 which further comprises an organic acid washing agent having a pH between about 2.7 and 4.0.

52. The combination of claim 51 wherein
(a) the chelating agent comprises a sodium salt of ethylenediaminetetraacetic acid;
(b) the dye comprises a basic dye;
(c) the membrane comprises an expoxy-fiberglass filter having a net positive surface charge; and
(d) the washing agent comprises acetic acid having a pH of about 3.

* * * * *

UNITED STATES PATENT AND TRADEMARK OFFICE
CERTIFICATE OF CORRECTION

PATENT NO. : 4,225,669
DATED : September 30, 1980
INVENTOR(S) : Joseph L. Melnick and Craig Wallis It is certified that error appears in the above-identified patent and that said Letters Patent are hereby corrected as shown below:

Column 3, line 33, "particular," should read --particularly,--.

Column 5, line 50, "sufficienty" should read --sufficiently--.

Column 8, line 29, "throgh" should read --through--.

Column 9, line 48, "because the" should read --because of the--.

Column 13, line 55, "Antiobiotic" should read --Antibiotic--.

Column 13, line 67, "antiobiotic." should read --antibiotic.--.

Column 19, Claim 40, line 1, "method of claim 37" should read
   --method of claim 36--.

Column 20, Claim 50, line 8, "1.0 um" should read --1.0 μm--.

Signed and Sealed this

Seventh Day of April 1981

[SEAL]

Attest:

RENE D. TEGTMEYER

*Attesting Officer*    *Acting Commissioner of Patents and Trademarks*